US009506883B2

(12) United States Patent
Takahashi et al.

(10) Patent No.: US 9,506,883 B2
(45) Date of Patent: Nov. 29, 2016

(54) SCALE DEPOSITION TESTING DEVICE

(71) Applicant: FUJI ELECTRIC CO., LTD., Kawasaki-shi, Kanagawa (JP)

(72) Inventors: Kuniyuki Takahashi, Tokyo (JP); Yoshitaka Kawahara, Kanagawa (JP)

(73) Assignee: FUJI ELECTRIC CO., LTD., Kanagawa (JP)

( * ) Notice: Subject to any disclaimer, the term of this patent is extended or adjusted under 35 U.S.C. 154(b) by 426 days.

(21) Appl. No.: 14/349,640

(22) PCT Filed: Jan. 17, 2013

(86) PCT No.: PCT/JP2013/050728
§ 371 (c)(1),
(2) Date: Apr. 3, 2014

(87) PCT Pub. No.: WO2013/114950
PCT Pub. Date: Aug. 8, 2013

(65) Prior Publication Data
US 2014/0254628 A1   Sep. 11, 2014

(30) Foreign Application Priority Data
Jan. 30, 2012 (JP) ................................ 2012-016204

(51) Int. Cl.
*G01N 25/00* (2006.01)
*G01K 13/00* (2006.01)
(Continued)

(52) U.S. Cl.
CPC .............. *G01N 25/00* (2013.01); *F03G 7/04* (2013.01); *G01F 1/00* (2013.01); *G01L 7/00* (2013.01); *G01N 33/1853* (2013.01); *Y02E 10/10* (2013.01)

(58) Field of Classification Search
USPC .............................. 374/7, 142, 143, 148, 165
See application file for complete search history.

(56) References Cited

U.S. PATENT DOCUMENTS 3,913,378 A * 10/1975 Hausler .................... G01B 7/06
374/7
4,044,605 A *  8/1977 Bratthall ............. G01M 3/3227
165/11.1

(Continued)

FOREIGN PATENT DOCUMENTS

| JP | 2002-213703 A | 7/2002 |
| JP | 2004-012303 A | 1/2004 |
| WO | WO 2010/038479 A1 | 4/2010 |

OTHER PUBLICATIONS

Ryuichi Itoi, et al.: "Study on Decrease of Reservoir Permeability Due to Deposition of Silica dissolved in Reinjection Water", Journal of the Geothermal Research Society of Japan, vol. 8, No. 3, (1986), pp. 229-241.

(Continued)

*Primary Examiner* — Mirellys Jagan
(74) *Attorney, Agent, or Firm* — Holtz, Holtz & Volek PC

(57) ABSTRACT

A scale deposition testing device, which is capable of precisely evaluating the state of scale deposition in consideration of an effect of retained geothermal water that occurs in an actual geothermal power plant, includes a plurality of scale deposition containers filled with particulates; hot water supply means for causing hot water to flow through each of the scale deposition containers; a retention unit for retaining the hot water; hot water condition change means for changing at least one of the flow rate, temperature, pressure, and composition of the hot water for each of the scale deposition containers; measuring means for measuring at least one of the flow rate, temperature, and pressure of the hot water flowing through each of the scale deposition containers; and a recorder for receiving data from the measuring means, the retention unit being capable of changing the hot water retention time.

14 Claims, 4 Drawing Sheets

(51) Int. Cl.
*F03G 7/04* (2006.01)
*G01N 33/18* (2006.01)
*G01F 1/00* (2006.01)
*G01L 7/00* (2006.01)

(56) References Cited

U.S. PATENT DOCUMENTS

| | | | | |
|---|---|---|---|---|
| 4,138,878 | A * | 2/1979 | Holmes | G01N 25/18 374/43 |
| 4,383,438 | A * | 5/1983 | Eaton | G01N 25/18 374/7 |
| 5,248,198 | A * | 9/1993 | Droege | F28F 19/00 374/43 |
| 5,429,178 | A * | 7/1995 | Garey | F28F 19/00 165/11.1 |
| 5,607,008 | A * | 3/1997 | Niederer | F24D 19/0092 165/11.1 |
| 5,762,128 | A * | 6/1998 | Counterman | F28F 27/006 165/11.1 |
| 6,062,069 | A * | 5/2000 | Panchal | G01N 33/2805 374/7 |
| 6,386,272 | B1 * | 5/2002 | Starner | G01B 21/085 165/11.1 |
| 7,594,430 | B2 * | 9/2009 | Beardwood | A61L 2/16 374/7 |
| 8,746,968 | B2 * | 6/2014 | Auret | G01N 25/18 374/29 |
| 2007/0025413 | A1 * | 2/2007 | Hays | A61L 2/16 374/7 |
| 2011/0239649 | A1 | 10/2011 | Myougan et al. | |
| 2013/0287063 | A1 * | 10/2013 | Kates | F24F 3/1603 374/143 |

OTHER PUBLICATIONS

Edward K. Mroczek, et al.: "Deposition of amorphous silica in porous packed beds—predicting the lifetime of reinjection aquifers" Geothermics 29 (2000), pp. 737-757 (in English).
International Search Report (ISR) dated Mar. 12, 2013 (and English translation thereof) issued in International Application No. PCT/JP2013/050728.
K.L. Brown, et al.: "pH Control of Silica Scaling", Proceedings of the New Zealand Geothermal Workshop, 1983, 5$^{th}$, pp. 157-161 (in English).

* cited by examiner

SCALE DEPOSITION TESTING DEVICE

TECHNICAL FIELD

The present invention relates to a scale deposition testing device that evaluates the state of scale deposition in which scale is deposited when hot water and the like resulting from geothermal power generation are reinjected into the ground.

BACKGROUND ART

In geothermal power generation, hot water collected from a production well (hereinafter referred to as geothermal water) is used to produce power. The geothermal water having been used to produce power is reinjected into the ground again.

Geothermal water contains greater amounts of calcium ion, dissolved silica, and the like than does well water and river water and hence tends to cause deposition of scale, such as calcium carbonate and amorphous silica. As a result, scale is deposited along a channel in a geothermal power plant and a well through which geothermal water having used to produce power is reinjected (hereinafter referred to as reinjection well), and the deposited scale narrows or otherwise blocks the channel, possibly resulting in an insufficient amount of reinjected hot water. If a sufficient amount of reinjected hot water is not provided, a reinjection well needs to be newly dredged, resulting in an increase in cost. Since the dredging cost risks the power generation business, the business risk increases if the degree of blockage of a reinjection well (blockage speed) cannot be estimated in advance.

In view of the fact described above, attempts to pre-evaluate the state of scale deposition have been made, as described in Non-patent Documents 1 and 2.

Non-patent Document 1 discloses that hot water is supplied to a filled layer made of a porous medium and the difference in pressure between the inlet and the outlet of the filled layer is determined to observe phenomena such as the change in coefficient of permeability of the filled layer due to scale deposition and the distribution of the amount of scale deposition along the distance.

Non-patent Document 2 discloses that hot water is allowed to flow through pipes having different diameters and the state of scale deposition is observed in each of the pipes.

PRIOR ART DOCUMENTS

Non-Patent Documents

[Non-patent Document 1] Itoi, Journal of the Geothermal Research Society of Japan, Vol. 8, No. 3, (1986) pp. 229-241

[Non-patent Document 2] E. K. Mroczek, Geothermics, 29, (2000) pp. 737-757

DISCLOSURE OF THE INVENTION

Problems to be Solved by the Invention

In an actual geothermal power plant, however, geothermal water collected from a production well may experience deposition, growth, and aggregation of silica in some cases until the geothermal water is reinjected into a reinjection well. It is therefore necessary to consider an effect of retained geothermal water that actually occurs in a geothermal power plant.

An object of the present invention is therefore to provide a scale deposition testing device capable of precisely evaluating the state of scale deposition in consideration of an effect of retained geothermal water that occurs in an actual geothermal power plant.

Means to Solve the Problems

A scale deposition testing device according to the present invention is characterized in including a plurality of scale deposition containers filled with particulates; hot water supply means for causing hot water to flow through each of the scale deposition containers; a retention unit that retains the hot water in a position upstream of the scale deposition container; hot water condition change means for changing at least one of the flow rate, temperature, pressure, and composition of the hot water for each of the scale deposition containers; measuring means for measuring at least one of the flow rate, temperature, and pressure of the hot water flowing through each of the scale deposition containers; and a recorder for receiving data from the measuring means, the retention unit being capable of changing the hot water retention time.

According to the present invention, filling each of the scale deposition containers with particulates that form the strata of a reinjection well or particulates having the same material composition as that of a pipe allows the scale deposition container to be considered as simulated strata that simulates the strata of the reinjection well or the inner wall of the pipe through which the hot water flows for evaluation of a scale occurrence situation in the hot water. Changing at least one of the flow rate, temperature, pressure, and composition of the hot water for each of the scale deposition containers, causing the produced hot water to flow through the scale deposition container, and measuring at least one of the flow rate, temperature, and pressure of the hot water allows simultaneous testing and evaluation of differences in scale occurrence situation that result from differences in characteristics of the hot water flowing into the scale deposition containers. Further, since the retention unit is capable of changing the hot water retention time and hence simulating the hot water retention time in an above-ground pipe and the like, the state of scale deposition can be precisely evaluated in consideration of an effect of retained geothermal water produced in an actual geothermal power plant.

The retention unit of the scale deposition testing device according to the present invention preferably includes a plurality of hot water retention tanks, a retention pipe that connects the hot water retention tanks to each other, and a bypass pipe that bypasses the hot water retention tanks. According to the aforedescribed aspect, the hot water retention time can be changed by switching the hot water channel between the channel in which the hot water flows through the retention pipe and the channel in which the hot water flows through the bypass pipe.

The retention unit of the scale deposition testing device according to the present invention preferably includes a hot water retention tank and a hot water amount adjuster that allows introduction of a heat-resistant material into the hot water retention tank to adjust the amount of hot water retainable in the hot water retention tank. The heat-resistant material is preferably a polytetrafluoroethylene ball. According to the aforedescribed aspect, the hot water retention time can be changed by introducing the heat-resistant material to adjust the amount of hot water retainable in the hot water retention tank.

The retention unit of the scale deposition testing device according to the present invention preferably includes a hot water retention tank in which a baffle plate is disposed to form a hot water channel and a plurality of hot water discharge ports provided along the hot water channel in the hot water retention tank. According to the aforedescribed aspect, since the baffle plate forms the hot water channel in the hot water retention tank, the hot water retention time can be changed by selecting the hot water discharging port as appropriate and discharging the hot water through the selected hot water discharging port.

The hot water condition change means of the scale deposition testing device according to the present invention is preferably a flow rate controller provided in a position upstream of each of the scale deposition containers. According to the aforedescribed aspect, the flow rate controller can adjust the flow rate of the hot water flowing into each of the scale deposition containers, whereby the scale occurrence situation, for example, for a variety of flow rates can be tested simultaneously for comparison evaluation.

The hot water condition change means of the scale deposition testing device according to the present invention is preferably a temperature adjuster for adjusting the temperature of the hot water flowing through each of the scale deposition containers. According to the aforedescribed aspect, differences in the scale occurrence situation, for example, for a variety of temperatures of the flowing hot water can be tested simultaneously for comparison evaluation.

The hot water condition change means of the scale deposition testing device according to the present invention is preferably a back pressure control valve provided in a position downstream of each of the scale deposition containers. According to the aforedescribed aspect, since the back pressure control valve provided in a position downstream of each of the scale deposition containers can change the pressure of the hot water in the scale deposition container, the scale occurrence situation for a variety of hot water pressure conditions can be examined.

The hot water condition change means of the scale deposition testing device according to the present invention is preferably a chemical adder that adds a chemical to the hot water flowing into the scale deposition container in a position upstream of at least one of the scale deposition containers. According to the aforedescribed aspect, hot water to which no chemical is added, hot water to which a chemical is added, and hot water to which different types of chemical are added, for example, can be simultaneously allowed to pass through the respective scale deposition containers for examination of changes in characteristics of the variety of types of hot water, and comparing the examination results allows evaluation of effects of the chemical injection.

The hot water supply means of the scale deposition testing device according to the present invention preferably includes a pressurizing pump for pressurizing the hot water flowing into the scale deposition container, a flowmeter that measures the flow rate of the hot water flowing through the scale deposition container, and a controller for performing feedback control on the pressurizing pump to adjust the flow rate of the hot water. According to the aforedescribed aspect, a scale occurrence situation, for example, in the hot water flowing through each of the scale deposition containers can be examined with the flow rate of the hot water flowing into the scale deposition container adjusted at a fixed value.

Each of the scale deposition containers of the scale deposition testing device according to the present invention is preferably so disposed that a hot water inflow port is disposed on the lower side thereof and a hot water outflow port is disposed on the upper side thereof. According to the aforedescribed aspect, gases degassed from the hot water are readily removed out of the scale deposition container.

In the scale deposition testing device according to the present invention, at least one of the scale deposition containers is preferably provided with a temperature adjuster that adjusts the temperature of the scale deposition container. According to the aforedescribed aspect, the temperature in the strata in an actual reinjection well or the temperature in an above-ground pipe in a geothermal power plant can be simulated.

The measuring means of the scale deposition testing device according to the present invention is preferably a pressure gauge provided in each position upstream and downstream of the scale deposition container. According to the aforedescribed aspect, a scale occurrence situation can be tracked by measuring the pressure of the hot water flowing into the scale deposition container and the pressure of the hot water flowing out of the scale deposition container and determining the difference between the pressures.

The scale deposition container of the scale deposition testing device according to the present invention is preferably provided with a plurality of pressure gauges along a direction in which the hot water flows. According to the aforedescribed aspect, scale deposition intensity and scale deposition range spreading in the scale deposition container can be detected in real time.

Advantageous Effects of the Invention

Any of the scale deposition testing devices according to the present invention allows precise evaluation of the state of scale deposition.

MODE FOR CARRYING OUT THE INVENTION

A scale deposition testing device according to the present invention will be described below with reference to the drawings.

Figure 1:
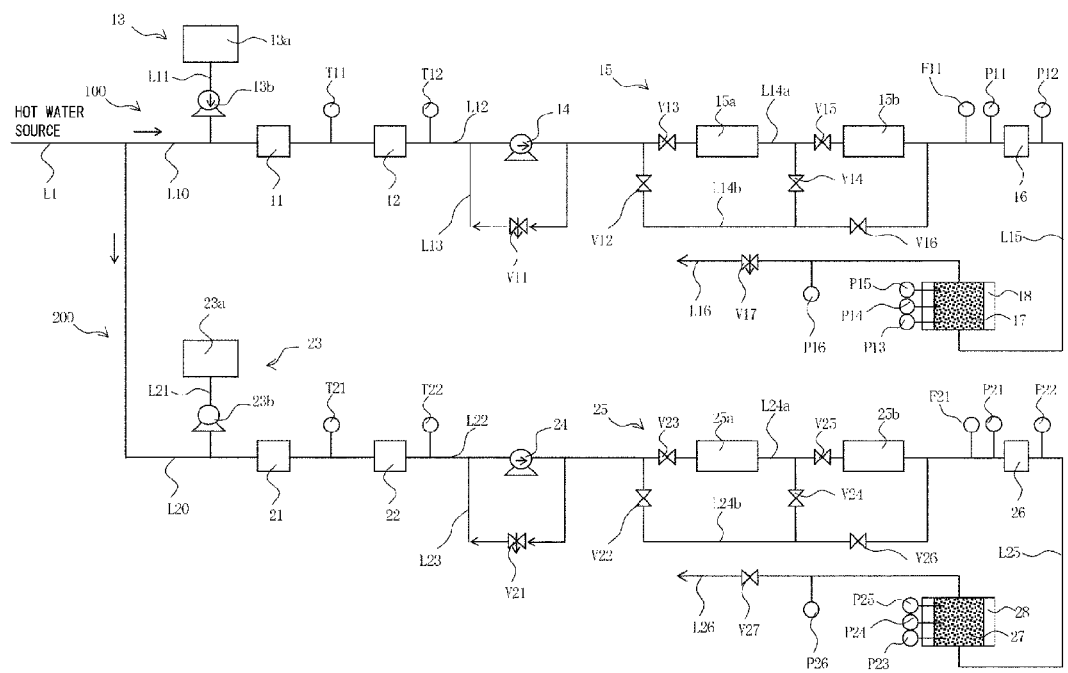
FIG. 1 is a schematic view of an embodiment of a scale deposition testing device according to the present invention.

FIG. 1 is a schematic view of an embodiment of the scale deposition testing device according to the present invention.

A pipe L1 extending from a hot water source is bifurcated into a pipe L10, which is directed to a first scale detection system 100, in which a scale deposition container 17 is disposed, and a pipe L20, which is directed to a second scale detection system 200, in which a scale deposition container 27 is disposed. The hot water source may be a production well in an actual geothermal power plant or a reservoir of hot water, simulating geothermal water, produced by adjusting the pH, composition, and temperature thereof to be equal to those of geothermal water collected from the production well.

In this embodiment, the first scale detection system 100 and the second scale detection system 200 have the same structure, and they will be collectively described.

A static mixer 11 (21) and a thermometer T11 (T21) are disposed on the pipe L10 (L20), which is bifurcated and extends from the pipe L1, and connected to a temperature adjuster 12 (22). A chemical adder 13 (23) is provided in a position upstream of the static mixer 11 (21) on the pipe L10 (L20).

The chemical adder 13 (23) includes a chemical storage tank 13a (23a), a chemical injection pipe L11 (L21), which extends from the chemical storage tank and is connected to the pipe L10 (L20), and a chemical liquid injection pump 13b (23b), which is attached to the chemical injection pipe L11 (L21) in an intermediate position thereof.

The temperature adjuster 12 (22) adjusts the temperature of hot water caused to flow into the scale deposition container 17 (27) and includes a heater, a cooler, or a heat exchanger. Adjusting the temperature of the hot water by using the temperature adjuster 12 (22) allows, for example, simulation of the temperature of the hot water before introduction of a binary power generator and the temperature of the hot water after the introduction and evaluation of an effect the introduction of the binary power generator.

A pipe L12 (L22) extends from the temperature adjuster 12 (22) and is connected to a hot water retention unit 15 (25). A thermometer T12 (T22) and a pressurizing pump 14 (24) are disposed on the pipe L12 (L22). Further, a bypass pipe L13 (L23), which circulates the hot water from a position downstream of the pressurizing pump 14 (24) to a position upstream of the pressurizing pump 14 (24), is attached to the pipe L12 (L22). A back pressure control valve V11 (V21) is disposed on the bypass pipe L13 (L23). In this embodiment, the back pressure control valve V11 (V21), the bypass pipe L13 (L23), and the pressurizing pump 14 (24) correspond to the "flow rate controller" in the present invention. Adjusting drive operation of the pressurizing pump 14 (24) and the opening of the back pressure control valve V11 (V21) to adjust the flow rate of the hot water that circulates through the bypass pipe L13 (L23) allows adjustment of the flow rate of the hot water that flows into the scale deposition container 17 (27).

The pressurizing pump 14 (24) increases the pressure of the hot water to prevent the hot water from flashing (evaporating) when the hot water passes through the scale deposition container 17 (27). A controller 51 performs feedback control on drive operation of the pressurizing pump 14 (24) and open and close operation of the back pressure control valve V11 (V21) based on a measurement from a flowmeter F11 (F21) disposed in a position downstream of the temperature adjuster 12 (22) (downstream of the hot water retention unit 15 (25) in this embodiment) in such a way that the measurement from the flowmeter F11 (F21) falls within a predetermined range.

The hot water retention unit 15 (25) includes, a retention pipe L14a (L24a), on which hot water retention tanks 15a (25a) and 15b (25b) are disposed, a pipe L14b (24b), which bypasses the hot water retention tanks 15a (25a) and 15b (25b), and channel switching valves V12 to V16 (V22 to V26), which are disposed on the retention pipe L14a (L24a) and the bypass pipe L14b (L24b). Providing the hot water retention unit allows simulation and evaluation of the hot water retention time in above-ground pipes and the like in the actual geothermal power plant. In this embodiment, two hot water storage tanks are provided, but three or more or only one hot water storage tank may be provided. Providing a plurality of hot water storage tanks allows fine adjustment of the hot water retention time, whereby the effect of the retention time can be precisely detected.

The flowmeter F11 (F21), a pressure gauge P11 (P21), a test piece 16 (26), and a pressure gauge P12 (P22) are disposed on a pipe L15 (L25), which extends from the hot water retention unit 15 (25), and the pipe L15 (L25) is connected to a hot water inflow port of the scale deposition container 17 (27). The test piece 16 (26) is a pipe made of the same material as that of pipes used in the geothermal power plant and disposed for evaluation of a scale occurrence situation in the pipe. A similar evaluation can be made by using a scale deposition container filled with particulates having the same material composition as that of the pipes used in the geothermal power plant, as will be described later. When no evaluation of pipe blocking is required, which occurs in some cases, a test piece need not be disposed.

In this embodiment, the scale deposition container 17 (27) has a hot water inflow port disposed on the lower side thereof and a hot water outflow port disposed on the upper side thereof. That is, the hot water flows through the scale deposition container 17 (27) from the lower side thereof toward the upper side thereof. Causing the hot water to flow through the scale deposition container 17 (27) from the lower side thereof toward the upper side thereof readily allows removal of gases originally dissolved in the hot water and degassed therefrom when the hot water passes through the scale deposition container 17 (27). When almost no gas is dissolved in the hot water, when the amount of gases degassed from the hot water is minute, or when the hot water flows at high speed (when the hot water flows at 1 m/s or faster, for example), the hot water may be allowed to flow through the scale deposition container 17 (27) from the upper side thereof toward the lower side thereof.

The scale deposition container 17 (27) is filled with particulates that form the strata of the reinjection well, such as beads and rocks, or particulates having the same material composition as that of the pipes used in the geothermal power plant. A scale deposition container filled with particulates that form the strata of the reinjection well can be considered as simulated strata that simulates the strata of the reinjection well and allows evaluation of a scale occurrence situation in the reinjection well. Further, a scale deposition container filled with particulates having the same material composition as that of the pipes can be considered as the inner wall of the pipe through which the hot water in the geothermal power plant flows and allows evaluation of a scale occurrence situation in the pipe.

In this embodiment, pressure gauges P13 to P15 (P23 to P25) are provided in the scale deposition container 17 (27) along the direction in which the hot water flows. Providing a plurality of pressure gauges along the direction in which the hot water flows allows real-time detection of scale deposition intensity and scale deposition range spreading in the scale deposition container.

A temperature adjuster 18 (28), which adjusts the temperature of the scale deposition container 17 (27), is provided around the outer circumference of the scale deposition container 17 (27). The temperature adjuster 18 (28) can adjust the temperature of the scale deposition container 17 (27) to simulate the temperature of the strata of the actual reinjection well or the temperature of the above-ground pipes in the geothermal power plant.

A pipe L16 (L26), on which a pressure gauge P16 (P26) and a back pressure control valve V17 (V27) are disposed, extends from the hot water outflow port on the upper side of the scale deposition container 17 (27) and is connected to a hot water outlet.

Figure 2:
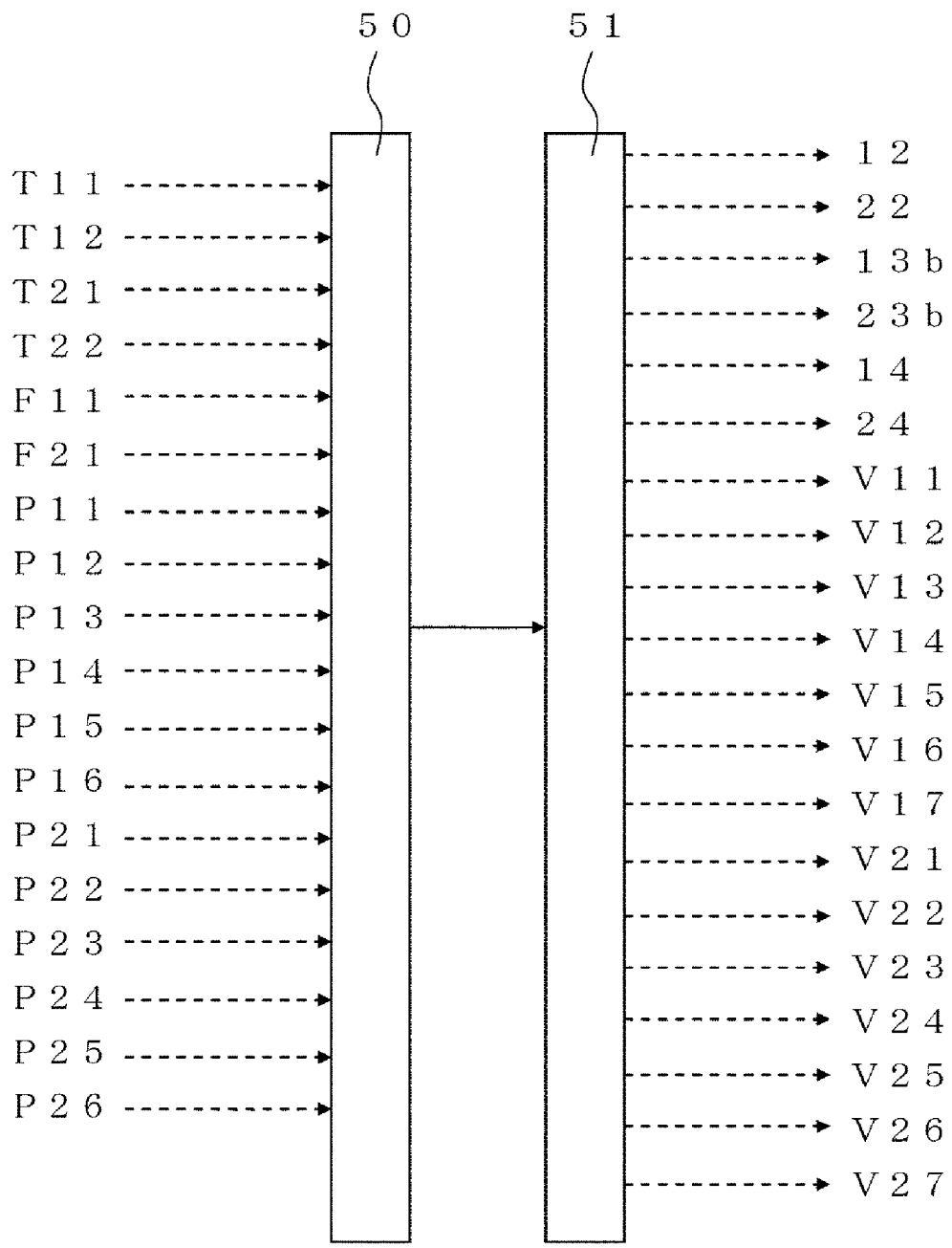
FIG. 2 is a schematic configuration diagram of a recorder and a controller of the scale deposition testing device.

Detection results from thermometer T11 (T12, T21, T22), the flowmeter F11 (F21), and the pressure gauge P11 (P12 to P16, P21 to P26) are inputted to a recorder 50 and recorded as measurement values along with measurement points of time, as shown in FIG. 2. The detection result from each of the measurement devices is further inputted to the controller 51. The controller 51 outputs signals according to the detection results to the temperature adjuster 12 (22), the chemical liquid injection pump 13b (23b), the pressurizing pump 14 (24), the back pressure control valve V11 (V21), the channel switching valves V12 (V13 to V16, V22 to V26), and the back pressure control valve V17 (V27) to control the operation thereof. Further, the recorder 50 also records output information from the controller 51, that is, operation situations of the temperature adjuster 12 (22), the chemical liquid injection pump 13b (23b), the pressurizing pump 14 (24), the back pressure control valve V11 (V21), the channel switching valves V12 (V13 to V16, V22 to V26), and the back pressure control valve V17 (V27).

In this embodiment, the pipes L1, L10, L12 to L15, L20, and L22 to L25, through which the hot water supplied from the hot water source flows, correspond to the "hot water supply means" of the present invention. Further, the chemical adder 13 (23) corresponds to a component that changes the composition of the hot water in the "hot water condition change means" of the present invention. The temperature adjuster 18 (28) corresponds to a component that changes the temperature of the hot water in the "hot water condition change means" of the present invention or. The back pressure control valve V11 (V21), the bypass pipe L13 (L23), and the pressurizing pump 14 (24) correspond to components that change the flow rate of the hot water in the "hot water condition change means" of the present invention. The pressurizing pump 14 (24) and the back pressure control valve V17 (V27) correspond to components that change the pressure of the hot water in "hot water condition change means" of the present invention or.

According to this scale deposition testing device, the hot water retention time can be readily changed by changing the channel of the hot water in the hot water retention unit 15 (25).

That is, in the hot water retention unit 15 (25), when the channel switching valves V13 (V23), V14 (V24), and V15 (V25) are closed and the channel switching valves V12 (V22) and V16 (V26) are opened, the hot water in the hot water retention unit 15 (25) is channeled through the channel that bypasses the hot water retention tanks 15a (25a) and 15b (25b). In this case, the hot water is not retained but is allowed to flow through the test piece 16 (26) and the scale deposition container 17 (27).

On the other hand, in the hot water retention unit 15 (25), when the channel switching valves V12 (V22) and V15 (V25) are closed and the channel switching valves V13 (V23), V14 (V24), and V16 (V26) are opened, the hot water in the hot water retention unit 15 (25) is channeled through the channel that goes through the hot water retention tanks 15a (25a). In this case, the hot water is allowed to flow through the test piece 16 (26) and the scale deposition container 17 (27) after retention time in which the hot water is retained in the hot water retention tanks 15a (25a) elapses.

Further, in the hot water retention 15 (25), when the channel switching valves V12 (V22), V14 (V24), and V16 (V26) are closed and the channel switching valves V13 (V23) and V15 (V25) are opened, the hot water in the hot water retention unit 15 (25) is channeled through the channel that goes through the hot water retention tanks 15a (25a) and 15b (25b). In this case, the hot water is allowed to flow through the test piece 16 (26) and the scale deposition container 17 (27) after retention time in which the hot water is retained in the hot water retention tanks 15a (25a) and 15b (25b) elapses.

Although the hot water retention time varies in some cases depending on the dimensions of the devices in the geothermal power plant, the scale deposition testing device according to the present invention allows the retention time to be readily changed without any change of the hot water retention tanks and other associated facilities whenever the hot water is retained. The scale deposition testing device according to the present invention can therefore simulate the hot water retention time in the above-ground pipes and the like in the actual geothermal power plant and evaluate the scale deposition situation.

The two scale detection systems are provided in this embodiment, but three or more scale detection systems may be provided. The respective scale detection systems are not necessarily same in their unit configuration. Further, having received measured data from thermometer T11 (T12, T21, T22), the flowmeter F11 (F21), and the pressure gauge P11 (P12 to P16, P21 to P26) and performed calculation according to the measured data, the controller 51 may transmit control signals to the temperature adjuster 12 (22), the chemical liquid injection pump 13b (23b), the pressurizing pump 14 (24), the back pressure control valve V11 (V21), the channel switching valves V12 (V13 to V16, V22 to V26), and the back pressure control valve V17 (V27) and also transmit the measured data and the control signal data along with measurement points of time to the recorder 50.

A description will next be made of examples of scale deposition tests using the scale deposition testing device according to the present invention.

(Evaluation of Effect of Chemical)

To evaluate an effect of a chemical, the chemical adder 13 is first used to add a chemical to the hot water that is supplied from the hot water source and flows into the first scale detection system 100. The static mixer 11 then mixes the hot water with the chemical, causes the mixture to flow through the temperature adjuster 12, the pressurizing pump 14, the hot water retention unit 15, and the test piece 16, and eventually supplies the hot water to the scale deposition container 17. The hot water having passed through the scale deposition container 17 is then delivered to the hot water outlet while the back pressure control valve V17 makes an adjustment in such a way that the pressure in the scale deposition container 17 becomes at a predetermined value.

On the other hand, no chemical is added to the hot water that flows into the second scale detection system 200 (that is, the chemical adder 23 is not activated), and the hot water with no chemical added is caused to pass through the temperature adjuster 22, the pressurizing pump 24, the hot water retention unit 25, and the test piece 26 and supplied to the scale deposition container 27. The hot water having passed through the scale deposition container 27 is then delivered to the hot water outlet while the back pressure control valve V27 makes an adjustment in such a way that the flow rate in the scale deposition container 27 becomes at a certain value. The temperature adjuster 22, the pressurizing pump 24, the hot water retention unit 25, and the back pressure control valves V21 and V27 are so adjusted that the temperature, pressure, flow rate, and the hot water retention time passing through the scale deposition container 27 to be equal to those of the hot water in the first scale detection system 100.

As described above, with the hot water caused to flow through the test piece and the scale deposition container, measurements from the pressure gauges provided in each of the scale detection systems are monitored for evaluation of the speed at which the test piece is blocked, the scale deposition intensity and the scale deposition range spreading in the scale deposition container, and the speed at which the scale deposition container is blocked. The speed at which the test piece is blocked can be determined based on the difference in pressure between the pressure gauge P11 (P21) provided in a position upstream of the test piece 16 (26) and the pressure gauge P12 (P22) provided in a position downstream thereof. The scale deposition intensity and the scale deposition range spreading in the scale deposition container can be determined based on measurements from the pressure gauges P13 to P15 (P23 to P25) provided in the scale deposition container 17 (27). The speed at which the scale deposition container is blocked can be determined based on the difference in pressure between the pressure gauge P12 (P22) provided in a position upstream of the scale deposition container 17 (27) and the pressure gauge P16 (P26) provided in a position downstream thereof.

Comparing measurement results on the items in the first scale detection system 100 with measurement results on the items in the second scale detection system 200 allows evaluation of an effect of the chemical injection.

Further, differentiating the type of chemical added to the hot water in the first scale detection system 100 from the type of chemical added to the hot water in the second scale detection system 200 allows evaluation of an effect of the type of chemical.

Moreover, differentiating the concentration of a chemical added to the hot water in the first scale detection system 100 from the concentration of the chemical added to the hot water in the second scale detection system 200 allows evaluation of an effect of the concentration of the chemical.

(Evaluation of Effect of Temperature of Hot Water)

To evaluate an effect of the temperature of the hot water, each of the temperature adjusters 12 and 22 in the scale detection systems is used to change only the temperature condition of the hot water flowing through the scale detection system, and the hot water is caused to flow through the test piece and the scale deposition container with the other conditions being the same. Measurement values from the pressure gauges provided in each of the scale detection systems are then monitored for evaluation of the speed at which the test piece is blocked, the scale deposition intensity and the scale deposition range spreading in the scale deposition container, and the speed at which the scale deposition container is blocked.

Comparing measurement results on the items in the first scale detection system 100 with measurement results on the items in the second scale detection system 200 allows evaluation of an effect of the temperature of the hot water. For example, an effect of introduction of a binary power generator can be evaluated.

(Evaluation of Effect of Flow Rate of Hot Water Passing Through Scale Deposition Container)

To evaluate an effect of the flow rate of the hot water passing through the scale deposition container, the drive operation of the pressurizing pump 14 (24) and the opening of the back pressure control valve V11 (V21) in each of the scale detection systems are so adjusted that the flow rate measured with the flowmeter F11 (F21) becomes at a predetermined value to change only the flow rate condition of the hot water passing through the scale detection system, and the hot water is caused to flow through the test piece and the scale deposition container with the other conditions being the same. Measurement values from the pressure gauges provided in each of the scale detection systems are then monitored for evaluation of the speed at which the test piece is blocked, the scale deposition intensity and the scale deposition range spreading in the scale deposition container, and the speed at which the scale deposition container is blocked.

Comparing measurement results on the items in the first scale detection system 100 with measurement results on the items in the second scale detection system 200 allows evaluation of an effect of the flow rate of the hot water passing through the scale deposition container.

(Evaluation of Effect of Pressure of Hot Water in Scale Deposition Container)

To evaluate an effect of the pressure of the hot water in the scale deposition container, the opening of the scale back pressure control valve V17 (V27) provided in a position downstream of the scale deposition container is adjusted to only change the pressure condition in the scale detection system, and the hot water is caused to flow through the test piece and the scale deposition container with the other conditions being the same. Measurement values from the pressure gauges provided in each of the scale detection systems are then monitored for evaluation of the speed at which the test piece is blocked, the scale deposition intensity and the scale deposition range spreading in the scale deposition container, and the speed at which the scale deposition container is blocked.

Comparing measurement results on the items in the first scale detection system 100 with measurement results on the items in the second scale detection system 200 allows evaluation of an effect of the pressure of the hot water in the scale deposition container.

Figure 3:
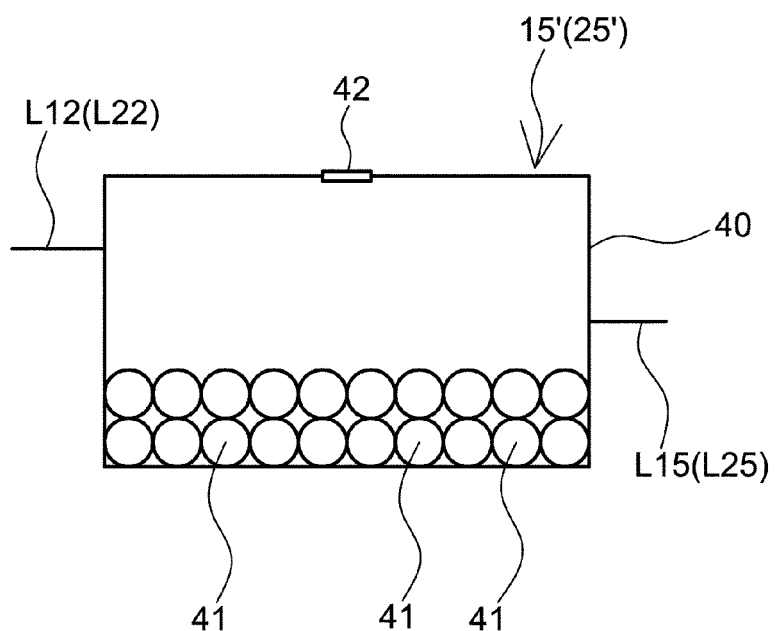
FIG. 3 shows another embodiment of a hot water retention unit of the scale deposition testing device.

FIG. 3 describes another embodiment of the hot water retention unit that can be used in the scale deposition testing device according to the present invention.

A hot water retention unit 15' (25') has a heat-resistant material dropping port 42 formed in an upper portion of a hot water retention tank 40. Dropping a heat-resistant material 41 through the heat-resistant material dropping port 42 in accordance with the hot water retention time allows adjustment of the amount of hot water retainable in the hot water retention tank 40.

That is, decreasing the amount of dropped heat-resistant material 41 to increase the amount of hot water retainable in the hot water retention tank 40 can prolong the hot water retention time. On the other hand, increasing the amount of dropped heat-resistant material 41 to decrease the amount of hot water retainable in the hot water retention tank 40 can shorten the hot water retention time.

The heat-resistant material 41 may be any material whose components neither elute nor deform, even when heated to 200° C. For example, a polytetrafluoroethylene ball is preferably used.

Figure 4:
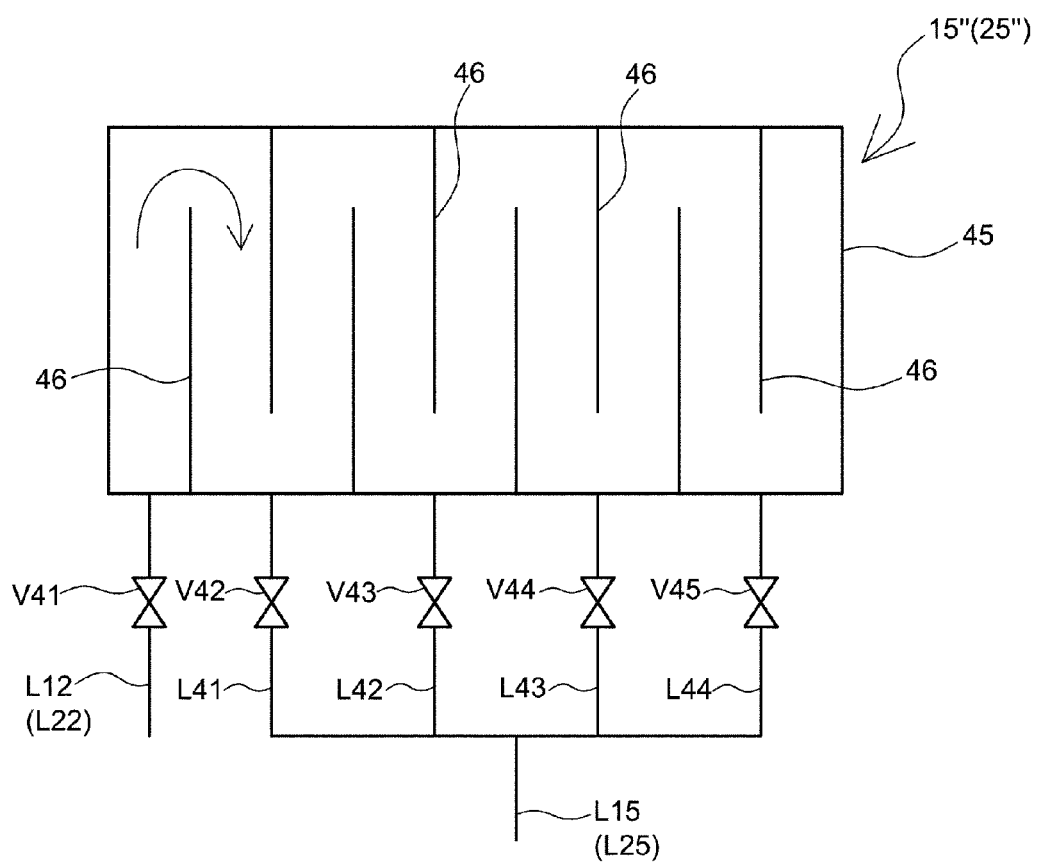
FIG. 4 shows still another embodiment of a hot water retention unit of the scale deposition testing device.

FIG. 4 describes still another embodiment of the hot water retention unit that can be used in the scale deposition testing device according to the present invention.

A hot water retention unit 15" (25") has a plurality of baffle plates 46 disposed in a hot water retention tank 45, and the baffle plates 46 form a hot water channel. Further, the pipe L12 (L22) is connected to the leading end of the hot water channel. An open/close valve V41 is attached to the pipe L12 (L22) in an intermediate position thereof. A plurality of hot water discharge ports (four in this embodiment) are provided along the hot water channel, and one end of a hot water discharge pipe L41 (L42, L43, L44) is connected to the corresponding one of the hot water discharge ports with an open/close valve V42 (V43, V44, V45)

attached to the hot water discharge pipe in an intermediate position thereof, the other end thereof being connected to the pipe L15 (L25).

The hot water retention unit 15" (25") can change the hot water retention time by changing the position where the hot water is discharged. That is, opening only the open/close values V41 and V42 and closing the other open/close valves shortens the hot water channel and hence the hot water retention time. On the other hand, opening only the open/close values V41 and V43 and closing the other open/close valves prolongs the hot water channel as compared with the case where only the open/close valves V41 and V42 are opened, and the hot water retention time can be prolonged accordingly.

EXPLANATION OF NUMERALS AND CHARACTERS 11, 21 Static mixer
12, 22 Temperature adjuster
13, 23 Chemical adder
13a, 23a Chemical storage tank
13b, 23b Chemical liquid injection pump
14, 24 Pressurizing pump
15, 15', 15", 25, 25', 25" Hot water retention unit
15a, 15b, 25a, 25b, 40, 45 Hot water retention tank
16, 26 Test piece
17, 27 Scale deposition container
18, 28 Temperature adjuster
50 Recorder
51 Controller
100 First scale detection system
200 Second scale detection system
F11, F21 Flowmeter
P11 to P16, P21 to P26 Pressure gauge
T11, T12, T21, T22 Thermometer
V11, V21 Back pressure control valve
V12 to V16, V22 to V26 Channel switching valve
V17, V27 Back pressure control valve
V41 to V45 Open/close valve

The invention claimed is:

1. A scale deposition testing device characterized in comprising:
   a plurality of scale deposition containers filled with particulates;
   hot water supply means for causing hot water to flow through each of the scale deposition containers;
   a retention unit that retains the hot water in a position upstream of the scale deposition containers;
   hot water condition change means for changing at least one of the flow rate, temperature, pressure, and composition of the hot water for each of the scale deposition containers;
   measuring means for measuring at least one of the flow rate, temperature, and pressure of the hot water flowing through each of the scale deposition containers; and
   a recorder for receiving data from the measuring means, the retention unit being capable of changing the hot water retention time.

2. The scale deposition testing device according to claim 1, wherein the retention unit includes a plurality of hot water retention tanks, a retention pipe that connects the hot water retention tanks to each other, and a bypass pipe that bypasses the hot water retention tanks.

3. The scale deposition testing device according to claim 1, wherein the retention unit includes a hot water retention tank in which a baffle plate is disposed to form a hot water channel and a plurality of hot water discharge ports provided along the hot water channel in the hot water retention tank.

4. The scale deposition testing device according to claim 1, wherein the hot water condition change means is a flow rate controller provided in a position upstream of each of the scale deposition containers.

5. The scale deposition testing device according to claim 1, wherein the hot water condition change means is a temperature adjuster for adjusting the temperature of the hot water flowing through each of the scale deposition containers.

6. The scale deposition testing device according to claim 1, wherein the hot water condition change means is a back pressure control valve provided in a position downstream of each of the scale deposition containers.

7. The scale deposition testing device according to claim 1, wherein the hot water condition change means is a chemical adder that adds a chemical to the hot water flowing into the scale deposition container in a position upstream of at least one of the scale deposition containers.

8. The scale deposition testing device according to claim 1, wherein the hot water supply means includes a pressurizing pump for pressurizing the hot water flowing into the scale deposition container, a flowmeter for measuring the flow rate of the hot water flowing through the scale deposition container, and a controller for performing feedback control on the pressurizing pump to adjust the flow rate of the hot water.

9. The scale deposition testing device according to claim 1, wherein each of the scale deposition containers is so disposed that a hot water inflow port is disposed on the lower side thereof and a hot water outflow port is disposed on the upper side thereof.

10. The scale deposition testing device according to claim 1, wherein at least one of the scale deposition containers is provided with a temperature adjuster for adjusting the temperature of the scale deposition container.

11. The scale deposition testing device according to claim 1, wherein the measuring means is a pressure gauge provided in each position upstream and downstream of the scale deposition containers.

12. The scale deposition testing device according to claim 1, wherein the scale deposition container is provided with a plurality of pressure gauges along a direction in which the hot water flows.

13. The scale deposition testing device according to claim 1, wherein the retention unit includes a hot water retention tank and a hot water amount adjuster that allows introduction of a heat-resistant material into the hot water retention tank to adjust the amount of hot water retainable in the hot water retention tank.

14. The scale deposition testing device according to claim 13, wherein the heat-resistant material is a polytetrafluoroethylene ball.

* * * * *